US012745906B2

(12) United States Patent
Jain et al.

(10) Patent No.: US 12,745,906 B2
(45) Date of Patent: Sep. 29, 2026

(54) BODY AREA NETWORK WITH TRANSMIT-ONLY DEVICES

(71) Applicant: Robert Bosch GmbH, Stuttgart (DE)

(72) Inventors: Vivek Jain, Sunnyvale, CA (US); Kaustubh Gandhi, Filderstadt (DE); Sushanta Mohan Rakshit, Milpitas, CA (US); Abhinav Kunchamwar, Stuttgart (DE)

(73) Assignee: Robert Bosch GmbH, Stuttgart (DE)

( * ) Notice: Subject to any disclaimer, the term of this patent is extended or adjusted under 35 U.S.C. 154(b) by 377 days.

(21) Appl. No.: 18/341,219

(22) Filed: Jun. 26, 2023

(65) Prior Publication Data

US 2024/0423472 A1 Dec. 26, 2024

(51) Int. Cl.
*A61B 5/00* (2006.01)
*H04W 4/38* (2018.01)
*H04W 84/18* (2009.01)

(52) U.S. Cl.
CPC ............. *A61B 5/0024* (2013.01); *H04W 4/38* (2018.02); *H04W 84/18* (2013.01)

(58) Field of Classification Search
CPC ...... A61B 5/0024; H04W 4/38; H04W 84/18; H04W 52/0216; H04W 72/0446; H04W 4/80; H04W 72/121; H04W 84/105; H04B 3/40; H04B 1/04; H02J 50/20
USPC .......................................................... 375/146
See application file for complete search history.

(56) References Cited

U.S. PATENT DOCUMENTS

| | | | | |
|---|---|---|---|---|
| 8,913,628 | B2 | 12/2014 | Patel et al. | |
| 11,457,490 | B2 | 9/2022 | Katan Baf Nezhad et al. | |
| 11,503,545 | B2 | 11/2022 | Katan Baf Nezhad et al. | |
| 2018/0167266 | A1 | 6/2018 | Subramani et al. | |
| 2019/0313352 | A1* | 10/2019 | Do | H04W 64/003 |
| 2019/0380583 | A1* | 12/2019 | Danneels | A61B 5/0024 |
| 2020/0169318 | A1 | 5/2020 | Kim et al. | |
| 2021/0204213 | A1 | 7/2021 | Lee et al. | |
| 2022/0386348 | A1 | 12/2022 | Zhang | |
| 2023/0284123 | A1 | 9/2023 | Ge et al. | |
| 2024/0163840 | A1 | 5/2024 | Säily et al. | |

OTHER PUBLICATIONS

Atmosic Technologies, "The Wolds Most Energy Efficient IoT Solutions: Product Portfolio", 2023, 6 pages.
Amjad et al., "Energy Efficient Resource Allocation for eHealth Monitoring Wireless Body Area Networks with Backscatter Communication", IEEE Sensors Journal, Aug. 2022, pp. 16638-16651, vol. 22, No. 16.

(Continued)

*Primary Examiner* — Fitwi Y Hailegiorgis
(74) *Attorney, Agent, or Firm* — BROOKS KUSHMAN P.C.

(57) ABSTRACT

Configuring and utilizing a body area network (BAN) is provided. In a configuration phase, configuration messages are sent for scheduling a plurality of transmit-only devices such that during a data collection phase each of the plurality of transmit-only devices is configured to transmit in an individually-assigned time slot. In the data collection phase, a data collector device receives, from the plurality of transmit-only devices, sensor data messages including sensor data from the transmit-only devices, the sensor data messages being scheduled according to the configuration phase.

20 Claims, 12 Drawing Sheets

(56) References Cited

OTHER PUBLICATIONS

Katanbaf et al., "Relacks: Reliable Backscatter Communication in Indoor Environments", Proc. ACM Interact. Mob. Wearable Ubiquitous Technology, Jun. 2020, pp. 1-24, vol. 4, No. 2, Article 48.
Khaleghi et al., "Radio Frequency Backscatter Communication for High Data Rate Deep Implants", IEEE Trans. On Microwave Theory and Techniques, Jul. 2018, 14 pages, vol. 67, No. 3.
Khan et al., "Wireless Power Transfer Techniques for Implantable Medical Devices: A Review", Sensors, Jun. 19, 2020, pp. 1-58, vol. 20, No. 3487.
Song et al., Advances in Wirelessly Powered Backscatter Communications: From Antenna/RF Circuitry Design to Printed Flexible Electronics, Proceedings of the IEEE, Jun. 18, 2021, pp. 1-22.
InPlay Inc., "InPlay's NanoBeacon Named RFID Journal's Best New Product of 2021" AP News, Sep. 30, 2021, 3 pages.
Ukkonen et al., "Backscattering-Based Wireless Communication and Power Transfer to Small Biomedical Implants", Proc. of SPIE, Feb. 21, 2020, 7 pages, vol. 11235.
Seymour, "Wake Bluetooth from Deep Sleep Using an RF Signal", Silicon Labs Live: Wireless Connectivity Tech Talks, Aug. 20, 2020, 32 pages.
Bosch, "BHI260AP Datasheet", Apr. 15, 2021, pp. 1-173.
Wikipedia, "Body Area Network", Jun. 22, 2023, 6 pages.
Wikipedia, "Carrier-Sense Multiple Access", Jul. 21, 2023, 3 pages.
Wikipedia, "Energy Harvesting", Jul. 31, 2023, 17 pages.
Wikipedia, "IEEE 802.15.6", Jun. 22, 2023, 2 pages.
Wikipedia, "Manchester Code", Jul. 31, 2023, 4 pages.
Wikipedia, "On-Off Keying", Jul. 31, 2023, 1 page.
Wikipedia, "Radio-Frequency Identification", Jul. 31, 2023, 31 pages.
Zang et al., "Throughput Improvement in Backscatter-Based Wireless Body Area Network", IEEE International Conference on Human-Machine Systems (ICHMS), Sep. 2020, 6 pages.
Zhang et al., "FreeRider: Backscatter Communication Using Commodity Radios", CoNEXT '17: Proceedings of the 13th International Conference on Emerging Networking Experiments and Technologies, Nov. 2017, pp. 389-401.
Priyankara et al., "A Clustering Method for Wireless Sensor Networks with Heterogeneous Node Types", IEICE Trans. Commun., Aug. 2011, vol. E94-B, No. 8, pp. 2254-2264.
Shiraishi et al., "Query Timing Analysis for Content-Based Wake-Up Realizing Informative IoT Data Collection", IEEE Wireless Communications Letters, Feb. 2023, vol. 12, No. 2, pp. 327-331.
Ullah et al., "MAC Hurdles in Body Sensor Networks", Advanced Communication Technology, Feb. 2009, pp. 1151-1155.

* cited by examiner

BODY AREA NETWORK WITH TRANSMIT-ONLY DEVICES

TECHNICAL FIELD

Aspects of the disclosure relate to the configuration and operation of body area networks to capture sensor data about a user.

BACKGROUND

A body area network involves communication between at least one body worn device and other body worn or external devices. Most applications fall into either personalized applications or medical applications. Personalized applications may include health, wellness, fitness, sports, etc., while medical applications have more stringent requirements with regards to data security, interoperability, and performance. To address body area network requirements for medical applications, there are several standardization efforts including the Institute of Electrical and Electronics Engineer (IEEE) 802.15.6 standard. On the other hand, for personalized applications there are no specific standards.

SUMMARY

In one or more illustrative examples, a method for configuring and utilizing a body area network (BAN) is provided. In a configuration phase, configuration messages are sent for scheduling a plurality of transmit-only devices such that during a data collection phase each of the plurality of transmit-only devices is configured to transmit in an individually-assigned time slot. In the data collection phase, a data collector device receives, from the plurality of transmit-only devices, sensor data messages including sensor data from the transmit-only devices, the sensor data messages being scheduled according to the configuration phase.

In one or more illustrative examples, a system for configuring and utilizing a body area network (BAN) includes a plurality of transmit-only devices and a data collector device. In a configuration phase, the plurality of transmit-only devices are configured to receive configuration messages for scheduling transmissions of the plurality of transmit-only devices, such that during a data collection phase each of the plurality of transmit-only devices is configured to transmit in an individually-assigned time slot. In the data collection phase, the data collector device is configured to receive, from the plurality of transmit-only devices, sensor data messages including sensor data from the transmit-only devices, the sensor data messages being scheduled according to the configuration phase.

DETAILED DESCRIPTION

As required, detailed embodiments of the present invention are disclosed herein; however, it is to be understood that the disclosed embodiments are merely exemplary of the invention that may be embodied in various and alternative forms. The figures are not necessarily to scale; some features may be exaggerated or minimized to show details of particular components. Therefore, specific structural and functional details disclosed herein are not to be interpreted as limiting, but merely as a representative basis for teaching one skilled in the art to variously employ the present invention.

Aspects of the disclosure relate to providing low power wireless connectivity among body worn devices as well as with non-body worn devices in communication with the body worn devices. Several applications such as health, wellness, fitness, sports, etc., require a user to wear one or more sensor devices on the body to provide sensor data. This sensor data may be utilized to measure and optimize properties such as posture correction, exercise monitoring/recommendation, sports performance, etc.

Body worn sensors are usually battery powered for optimal user experience and, in some cases, required by application itself. Because body worn devices are generally battery powered, a tradeoff between power consumption and data rate/latency remains a key challenge. Hence, low power consumption is very important, along with satisfying data rate, latency, and interoperability requirements.

In this disclosure, sensors with transmit-only radios are used. Such devices may lead to an order of magnitude power savings for wireless communication compared to transceiver-based solutions. Depending on the use case, these transmit-only sensors may allow the sensors to be completely battery-less. The management of several transmit-only sensors and supporting quality of service requirement of the application is non-trivial. Further aspects of the disclosure present methods to support those requirements.

Figure 1:
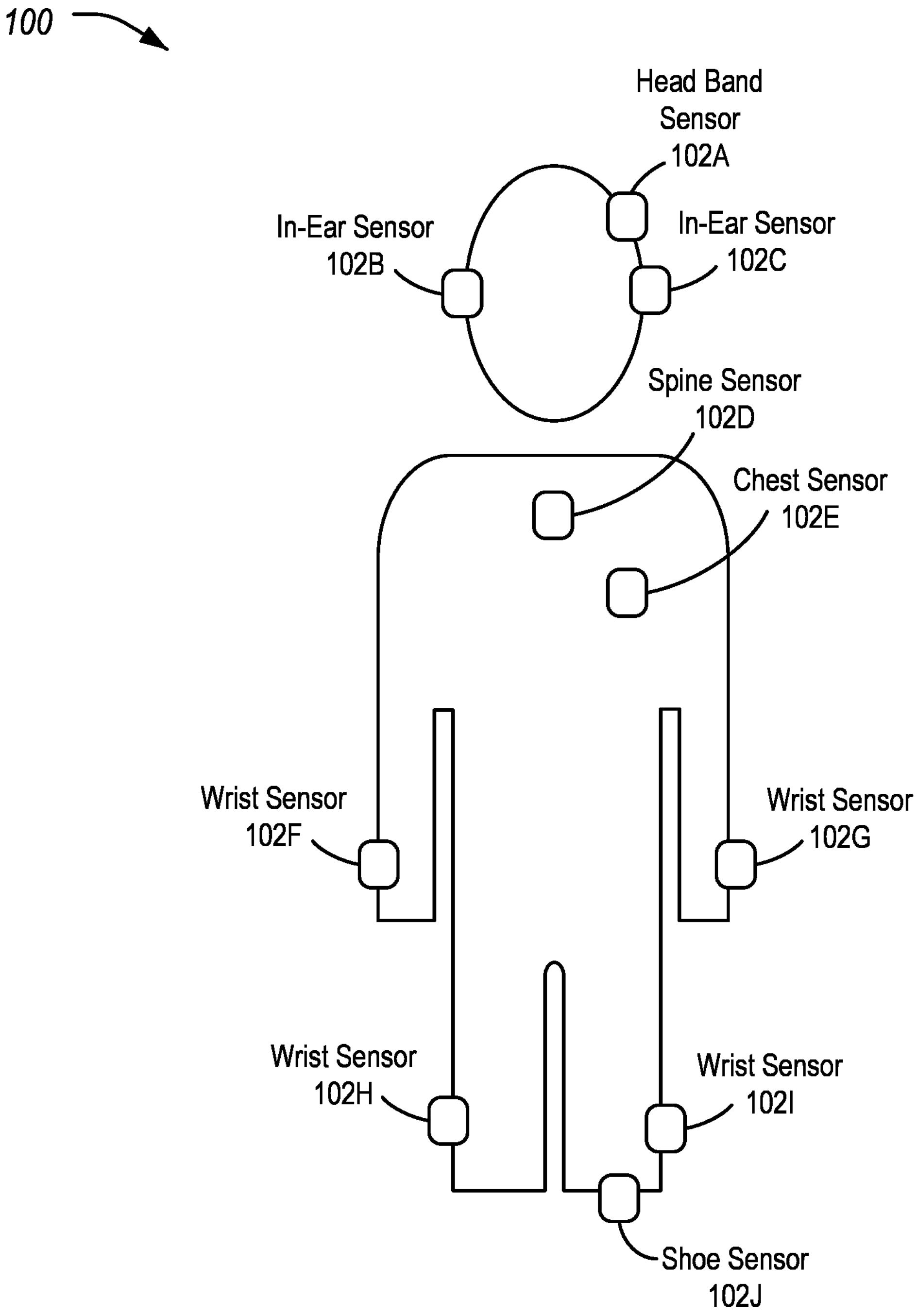
FIG. 1 illustrates an example application where a person is wearing several sensors on the body.

FIG. 1 represents an application in which a user is wearing several sensors 102 on the body. These sensors 102 may be placed directly on human body (e.g., with or without a casing) or may be embedded in body worn objects such as clothing, shoes, etc. As shown, the user is wearing a headband sensor 102A on the user's head. The user is also wearing in-ear sensors 102B, 102C in either ear. The user also has a spine sensor 102D located on the user's spine, and a chest sensor 102E located on the user's chest. The user also has wrist sensors 102F, 102G on each wrist and ankle sensors 102H, 102I on either ankle. The user also has a shoe sensor 102J in the user's shoe. It should be noted that these sensors 102 are merely examples, and more, fewer, or differently located sensors 102 may be used.

At least one of those sensors 102 may utilize a transmit-only radio. A transmit-only radio may be configured to send transmissions but not also receive transmissions. The transmit-only radio therefore be able to operate in a much lower power mode than a transceiver that also is configured to receive transmissions.

In some examples, one or more of the sensors 102 may support wakeup radio. Wakeup radio refers to systems in which a receiver is configured to wake up just in time to receive radio transmissions. This may be accomplished through adding a small companion receiver, with the purpose of waking up the primary connectivity radio. The small companion receiver may be referred to as a wakeup receiver. Since the wakeup receiver may only need to detect presence of a wakeup signal, and not decode complex information, the wakeup receiver may be implemented in a lower power design than a full receiver.

As a specific example, the sensors 102 may implement BLUETOOTH low energy (BLE), e.g., as a BLE transceiver with wakeup radio and/or as BLE transmit-only devices. Such radios are low power compared to traditional BLE implementations, while still being able to create and transmit BLE packets. A wakeup radio BLE transmitter in general consumes less extra energy compared to a BLE backscatter solution, yet can create standard complaint transmit packet without needing any excitation signal for data transfer. Such transmit-only devices may still need a wakeup signal for the wakeup radio. It should be noted that use of BLE is only an example, and the sensors 102 may implement other wireless technologies including Wi-Fi, IEEE 802.15.4, ultra-wideband (UWB), various proprietary protocols, etc.

The sensors 102 may be powered by a power source such as a super-capacitor or a battery. In some cases, the sensors 102 may scavenge energy from ambient conditions. It should be noted that various wireless charging methods may be utilized during usage of the sensor 102 devices on the human body. After the usage, the sensors 102 may be recharged or the batteries replaced.

Figure 2A:
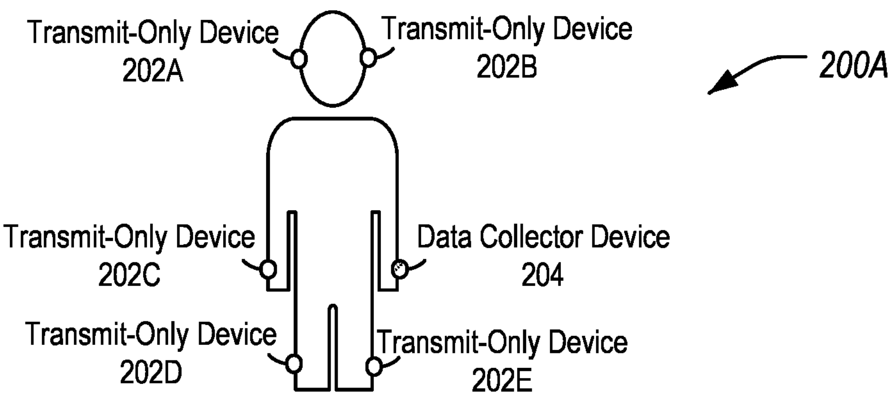
FIG. 2A illustrates a first body area network architecture in which the sensors and data collector are on the body.
Figure 2B:
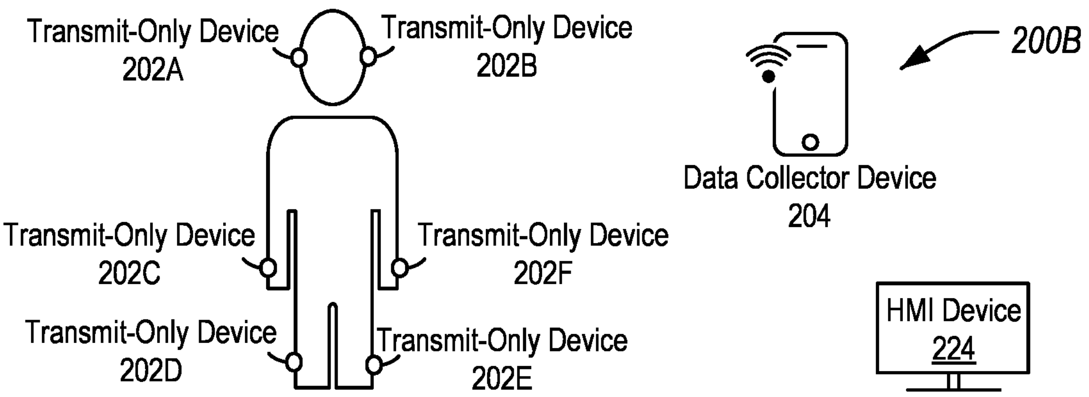
FIG. 2B illustrates a second body area network architecture in which the sensors are on body and the data collector is an external device.
Figure 2C:
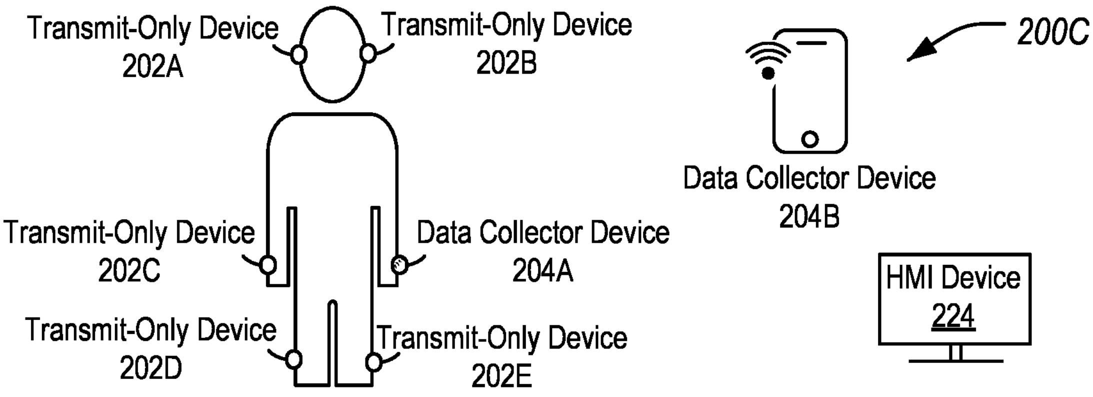
FIG. 2C illustrates a third body area network architecture having multiple collectors on and off the body, in combination with sensors on the body.
Figure 2D:
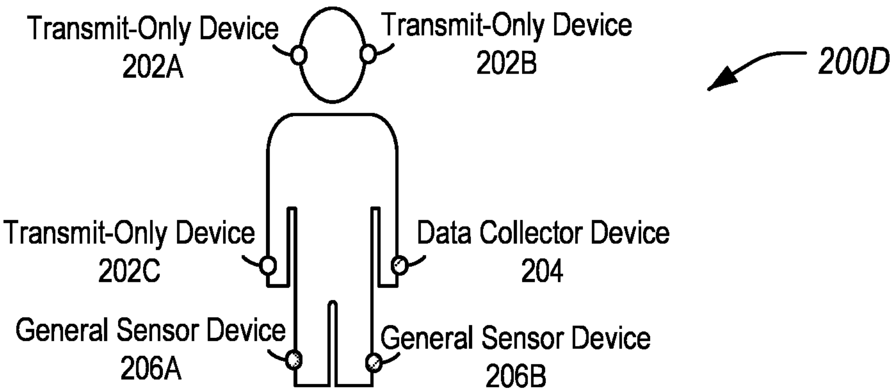
FIG. 2D illustrates a fourth body area network architecture having general sensor devices configured to receive and transmit in addition to the transmit-only devices.

FIGS. 2A-2D illustrate examples of a BAN 200 system architectures. FIG. 2A illustrates a first body area network 200A architecture, in which transmit-only devices 202A-E (collectively transmit-only devices 202) and a data collector device 204 are located on the body. FIG. 2B illustrates a second body area network 200B architecture, in which only transmit-only devices 202A-F are on body and the data collector device 204 is an external device. FIG. 2C illustrates a third body area network 200C architecture, having multiple data collector devices 204A, 204B both on and off the body, in combination with transmit-only devices 202A-E on the body. FIG. 2D illustrates a fourth body area network 200D, having general sensor devices 206 configured to both receive and transmit, in addition to the transmit-only devices 202. While not specifically called out in FIGS. 2A-2D, it should be noted that the transmit-only devices 202 and general sensor devices 206 generally include sensors 102 as discussed above.

Figure 2E:
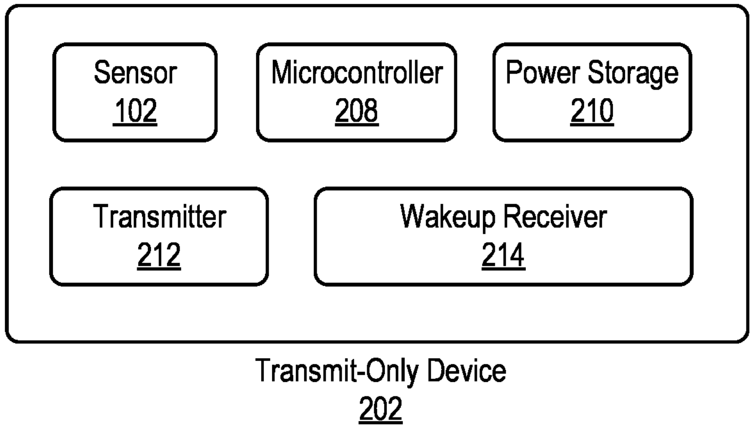
FIG. 2E illustrates further aspects of an example transmit-only device.

FIG. 2E illustrates further aspects of an example transmit-only device 202. As shown, the transmit-only device 202 may include at least one sensor 102, a microcontroller 208 including a microprocessor, memory and I/O to connect with other peripherals, a power storage 210, a transmitter 212, and an optional wakeup receiver 214. The sensors 102 may include inertial measurement units (IMUs) (such as an accelerometer or a gyroscope), a pressure sensor, an optical sensor, etc. These sensors could be co-located or could be distributed on the body in an area of interest such as hand, chest, back, etc.

The microcontroller 208 may be utilized to generate data packet and process sensor data. Additionally, the sensors 102, microcontroller 208, radio transmitter 212, and wakeup receiver 214 may be separate chips, circuits, devices, or packaged in one module. The transmitter 212 may be configured to transmit signals using various protocols such as BLE, Wi-Fi, IEEE 802.15.4, UWB, various proprietary protocols, etc.

The transmit-only device 202 may be powered by the power storage 210. The power storage 210 may be a normal battery, a super capacitor, or a rechargeable battery. For rechargeable power options, the device may additionally utilize wired, wireless charging or ambient charging, power harvesting from kinetic energy, etc.

The transmit-only device 202 may optionally include a wakeup receiver 214. The wakeup receiver 214 circuit may allow the transmit-only device 202 to receive a wakeup message (via a wakeup signal) or to transmit data packets. The wakeup signal may be provided using a simple On-Off Keying. One such implementation utilizes Manchester coded 125 kHz waveform. The transmitted data packet signal may be of standard technologies such as BLE, Wi-Fi, IEEE 802.15.4, 5G reduced capacity, or any other proprietary wireless protocol. The transmit-only device 202 may optionally utilize wakeup circuitry comprising an envelope detector at a minimum to wake up only when signal is above a given threshold. The transmit-only device 202 may also include a pattern correlator to wake up only when message is addressed to the transmit-only node by utilizing a unique pattern for each transmit-only device 202.

Figure 2F:
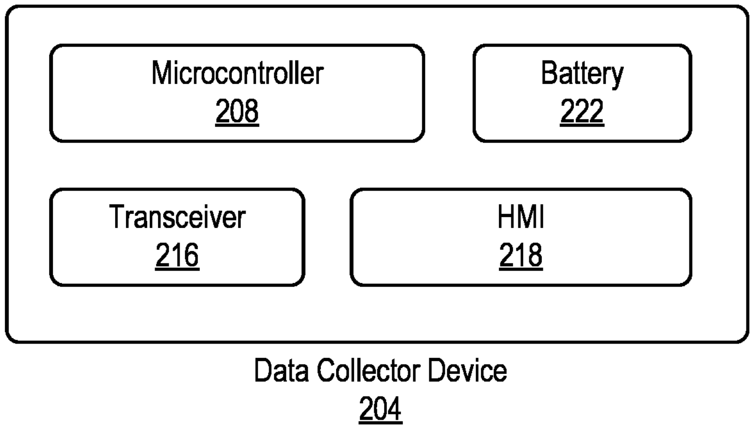
FIG. 2F illustrates further aspects of an example data collector device.
Figure 2G:
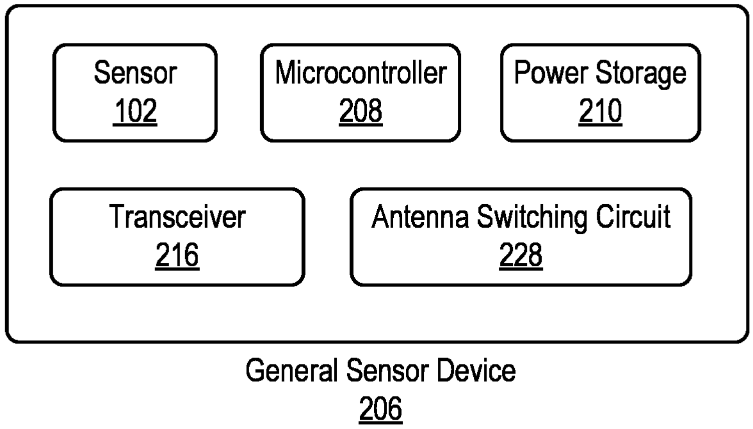
FIG. 2G illustrates further aspects of an example general sensor device.

When a wakeup receiver 214 is employed, a transmit-only device 202 may also include an antenna switching circuit 228 (shown in FIG. 2G but not in FIG. 2E). The antenna switching circuit 228 may allow the transmit-only device 202 to switch between a transmit mode in which the transmitter 212 is utilized and a receiving mode in which the wakeup receiver 214 is active. When the antenna switching circuit 228 is in transmit mode, the transmit-only device 202 may transmit raw or processed sensor data using the radio transmitter 212. The antenna switching circuit 228 by default remains in receiving mode to receive the wakeup pattern (e.g., when not transmitting). The transmit-only device 202 may also employ machine learning and advance signal processing techniques to process application-specific data directly as derived from sensors 102, such as step counting, personalized fitness tracking, swim analytics, pedestrian always-on position tracking, etc. The transmit-only device 202 may also include additional human machine interface (HMI) components, such as light emitting diodes (LEDs), haptics, etc., for providing user feedback.

FIG. 2F illustrates further aspects of an example data collector device 204. The data collector device 204 may be placed on the body in some examples, but off the body in others. The data collector device 204 may be used to receive and aggregate data from multiple transmit-only devices 202. The data collector device 204 may include a wireless transceiver 216 to receive the transmitted data. The wireless transceiver 216 may use the same wireless technology as the transmit-only devices 202 and/or as other on-body general sensor devices 206 which use a wireless transceiver 216. In addition to the wireless transceiver 216 being able to use user the same wireless technology as the transmit-only devices 202, the wireless transceiver 216 may also support additional wireless technologies such as Wi-Fi, BLE, IEEE 802.15.4, cellular, etc., to allow the data collector device 204 to communicate with additional HMI devices 224 such as televisions, display screens, or tablet computing devices. Further (while not shown) in some examples this wireless transceiver 216 may only employ receiver circuitry to receive the data packets from transmit-only devices 202 to reduce power consumption, device size, and cost.

For an optimal or immersive user experience, the data collector device 204 may include an HMI 218 to provide for user feedback. The data collector device 204 may also include a microcontroller 208 to aggregate and process sensor data for displaying or forwarding to the HMI devices 224. The data collector device 204 itself may be battery powered and may employ a rechargeable battery 222 which may be charged via wired or wireless means.

FIG. 2G illustrates further aspects of an example general sensor device 206. Similar to the transmit-only device 202, the general sensor device 206 may include at least one sensor 102, a microcontroller 208 including a microprocessor, memory and I/O to connect with other peripherals, and a power storage 210. However, the general sensor device 206 may include a transceiver 226 instead of only transmitter 212. It should be noted that, in some cases, the transmit-only device 202 and the general sensor device 206 may be configurations of a single device. For instance, some such devices may be able to reconfigure as being either a transmit-only device 202 or a general sensor device 206.

The antenna switching circuit 228 may allow the general sensor device 206 to switch between receiving a wakeup message (via a wakeup signal) or transmitting data packets. When the antenna switching circuit 228 is in wakeup mode, the general sensor device 206 may be able to receive wakeup signals via the wireless transceiver 216. When the antenna switching circuit 228 is in transmit mode, the transmit-only device 202 may transmit raw or processed sensor data using the wireless transceiver 216. This may allow the general sensor devices 206 to either operate as discussed above with respect to the wakeup circuit 214 of the transmit-only device 202 or to operate as discussed above using the wireless transceiver 216 of the data collector device 204.

Figure 3:
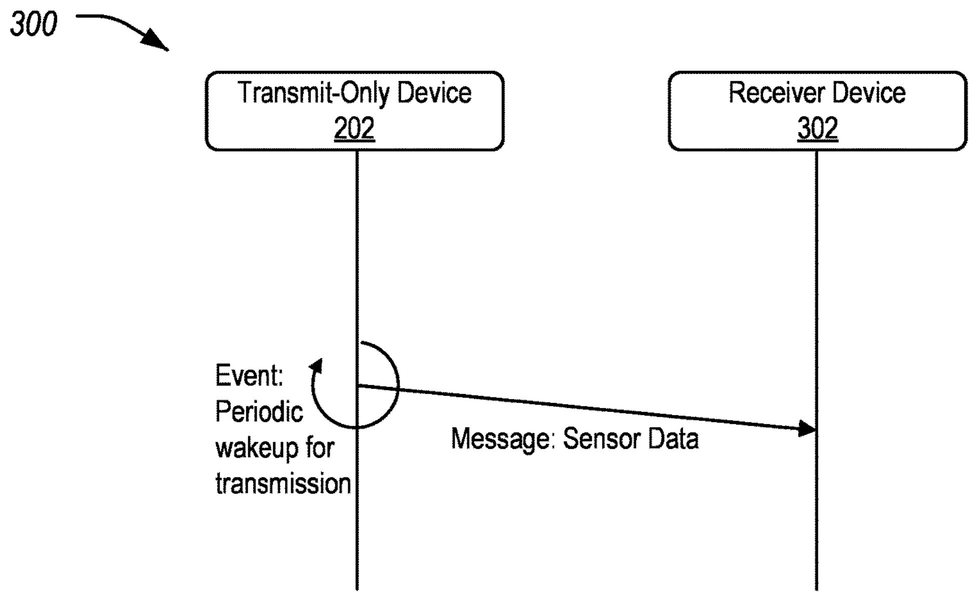
FIG. 3 illustrates an example of a predetermined periodic wakeup of a transmit-only device.

The devices in the BAN 200 may take on various roles. As shown in FIG. 3, these roles may include a receiver device 302. A body area network 200 with transmit-only devices 202 includes at least two main devices: at least one transmit-only device 202 having a sensor 102 and a receiver device 302 configured to operate as a receiver of the transmissions from the sensor 102. For complex functionality a network may include several transmit-only devices 202 or a combination of several transmit-only devices 202 and general sensor devices 206 (i.e., devices with wireless transceivers 216).

Figure 4:
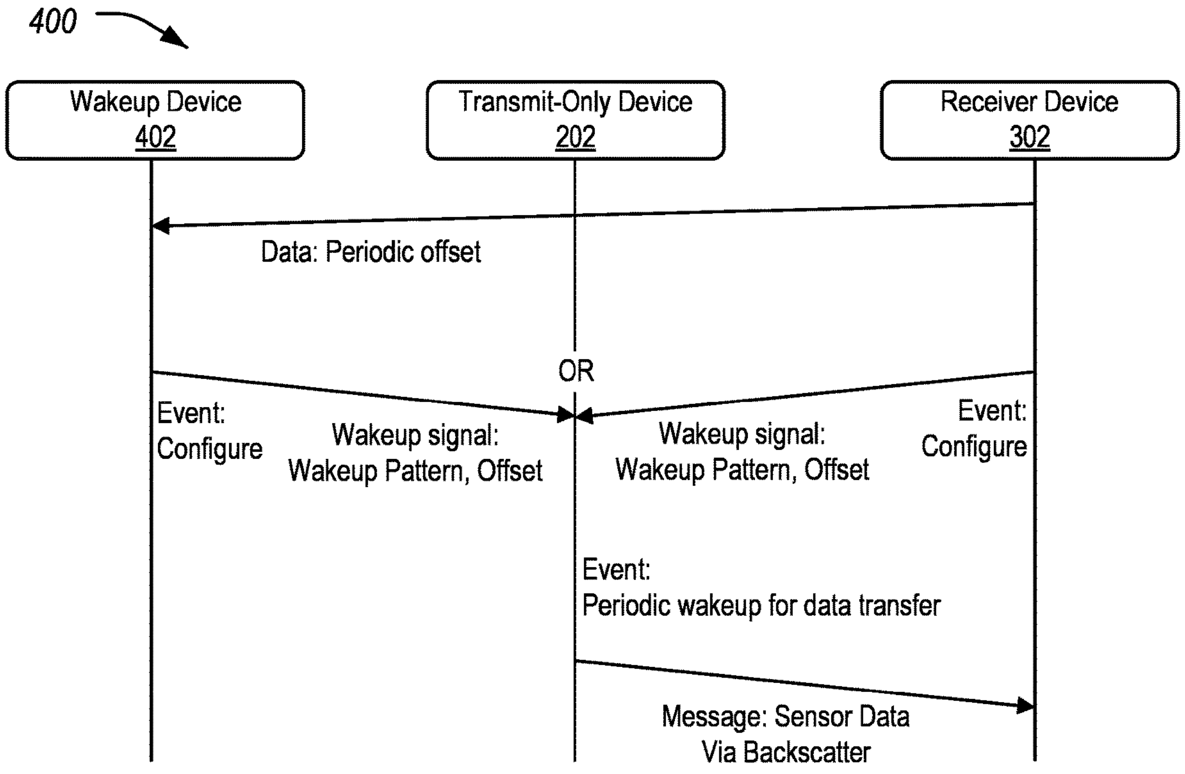
FIG. 4 illustrates an example of an optimized periodic wakeup using channel arbitration techniques.

As shown in FIG. 4, these roles may also include a wakeup device 402. The wakeup device 402 may be configured to provide the wakeup signal to wakeup radios of the transmit-only devices 202. As noted above, the wakeup signal may be provided using a simple On-Off Keying.

One or more devices of the body area network 200 may implement the wakeup device 402 role. In one example, the wakeup device 402 may be implemented by one of the sensors 102. Or the data collector device 204 may serve as the wakeup device 402. In another example, the wakeup device 402 may be implemented as a dedicated device for generating the wakeup signal. In yet another example, the HMI device 224 may be used to generate the wakeup signal. For a more immersive or enhanced user experience, the BAN 200 may include such additional HMI devices 224 such as a smartphone, tablet, tv, connected screens, etc. The receiver device 302 may also be used to generate the wakeup signal to configure the transmit-only devices 202.

Standard wearable devices such as smartwatches, rings, etc., may also operate as the data collector device 204. When a separate HMI device 224 is used, the data collector device 204 may simply act as a sensor 102 while the HMI device 224 may operate as receiver device 302 for all sensor data from general sensor devices 206 and transmit-only devices 202. Alternately, the HMI device 224 may generate the wakeup signal while the data collector device 204 acts as the receiver device 302. The data collector device 204 itself may generate the wakeup signal to configure transmit-only devices 202 and act as the receiver device 302 during data communication cycles.

The BAN 200 may collectively enable logging and/or analyzing of data from the sensors 102 for various applications. These applications may include, as some non-limiting examples: body motion capture application for orientation tracking like Yoga or curvature tracking such as running; posture correction and balancing; daily activities such as walking, running, biking, sleeping, etc.; fitness activities such as (full body) workouts, exercises, etc.; wellbeing activities such as yoga, dancing, meditation, etc.; sports activities such as soccer, boxing, basketball, cricket, badminton, tennis, table tennis, golf swing, swimming, etc.; and/or custom gestures such as pet activities (scratching), accessories (ring), skateboard, smartphone photo/QR-code scan, etc.

Referring again to FIG. 3, an example of a predetermined periodic wakeup of a transmit-only device 202 is illustrated. The transmit-only device 202 may transmit sensor data when it has data to transmit, or may periodically transmit responsive to expiration of a timer for transmission as shown.

For the periodic transmission, each transmit-only device 202 may collect sensor data 304 for a pre-determined period of time such that when the timer expires, the transmit-only device 202 transmits the sensor data 304. This period of time may be random, in an example. The periodic interval time information may also be included in the data message, or the data collector device 204 may receive a first few initial messages from each transmit-only device 202 to infer its respective periodic time interval.

For the random transmission, each transmit-only device 202 may collects data for a random period of time, such that once the timer expires the transmit-only device 202 transmits the data along with a time interval for the next round of transmission. In an alternative, the transmit-only device 202 may also wake up randomly and decide whether to transmit based on a random probability (e.g., taken from a uniform distribution between 0 and 1). If the probability is above a predefined threshold, e.g., 1/n where n is total number of transmit-only devices 202, then the transmit-only device 202 may transmit, otherwise the transmit-only device 202 may not transmit. Responsive to the transmit-only device 202 determining not to transmit, the transmit-only device 202 may wait for a shorter random time again before calculating the probability for transmission. The method is similar to p persistent carrier sense multiple access (CSMA).

These approaches may be sufficient when the number of transmit-only devices 202 is small and network utilization is low. However, if high data rates are desired to be supported, additional methods may be utilized to perform channel arbitration.

One approach is to include a low power wakeup receiver 214 in each of the transmit-only devices 202. The wakeup circuit may trigger the transmit-only device 202 to transmit responsive to receiving a wakeup signal above a predefined threshold signal level. This may address the issue of transmitting to be performed only at times requested by the receiver of the data collector device 204. With transmission power control, it can therefore be ensured that only transmit-only devices 202 on the human body will wake up and transmit. This approach may be acceptable if there is only a single transmit-only device 202 on the body.

However, in case of many transmit-only devices 202, an additional approach for channel arbitration may be desired to ensure that messages can be received from all of the transmit-only devices 202. Otherwise, energy in transmitting may be wasted if those messages are ignored or overlap or are otherwise unable to be received. This channel arbitration may be performed in various ways, such as those indicated below. One of more of these channel arbitration approaches may be combined to further improve performance with multiple transmit-only devices 202.

In one channel arbitration approach, each transmit-only device 202 may randomly decide whether to transmit or not to transmit (e.g., when the transmit-only device 202 has data to transmit). The transmit-only device 202 may not need to transmit when it has no data to send, unless the time between last transmission exceeds a pre-determined sending timeout. In that case, the transmit-only device 202 may still transmit a message to indicate that the transmit-only device 202 is still alive.

In another channel arbitration approach, each transmit-only device 202 may transmit on a different channel, so either at receiver we have multiple receivers (e.g., operating on different channels) or a software radio that can receive all transmit-only messages simultaneously. Or the receiver may decide which transmitting device to tune in. In this case, energy may be expended for transmitting nodes that are unnecessary to be listened to.

In another channel arbitration approach, a node identifier (ID) may be coded in the wakeup signal which is detected by the pattern correlator at the receiver. This may allow the indicated transmit-only node to respond while the other transmit-only devices 202 ignore the wakeup message.

FIG. 4 illustrates an example of an optimized periodic wakeup using channel arbitration techniques. For instance, a time offset may be piggybacked in the wakeup pattern along with node ID to inform the transmit-only device 202 about its time period for transmission. During normal transmission, the BAN 200 does not require to include a wakeup pattern, thereby reducing energy consumption and enhancing system capacity. To offset normal clock drifts, such configuration messages may be sent from time to time. This configuration message may be sent from either the dedicated device sending the wakeup signal or from the receiver itself.

As shown, the receiver device 302 may send a periodic offset to the wakeup device 402. The wakeup device 402 may then send a configure event to the transmit-only device 202, which may include a wakeup signal having a wakeup pattern and/or the periodic offset. In the alternative, the wakeup device 402 may send the configure event to the transmit-only device 202, which may include a wakeup signal having a wakeup pattern and/or the periodic offset. Responsive to the periodic wakeup for the data transfer occurring, the transmit-only device 202 may send the message data.

FIGS. 5A-5I illustrates aspects of a system protocol design and message formats including message scheduling. Two approaches are discussed: a no pipeline, single radio architecture and a pipeline enabled, dual radio architecture.

In the no pipeline, single radio architectures, the receiver device 302 is assumed to have only one radio and hence all devices are scheduled sequentially. Initially a configuration phase is performed where the controller device sends the Beacon C (configuration) messages to configure at least the transmit-only devices 202. During the configuration phase, each of the general sensor devices 206 and transmit-only devices 202 is scheduled, such that during a data collection phase each of them can transmit in their individual assigned/calculated time slots. In case a dedicated source is being used for generating wakeup signal, this beacon may be used to synchronize that device as well.

In the pipeline enabled, dual radio architecture, two radios are assumed for reception: one for general sensor devices 206 and one for transmit-only devices 202. The advantage of such an architecture is that when general sensor devices 206 are being configured, transmit-only devices 202 may be configured in parallel (i.e. pipelined) on a separate channel. Another advantage is a shorter duration of the data collection phase. Here again, the general sensor devices 206 and transmit-only devices 202 may be scheduled for each receiving radio. Thus, the system capacity can be doubled at a cost of one additional radio at the receiver. An alternate setup may utilize a collector for collecting data from all general sensor devices 206 with an HMI/display device from all transmit-only devices 202 (or vice versa) with the data being aggregated at either end for analytics and/or user experience (UX).

The key messages for these architectures may include Beacon C messages, configuration messages, Beacon D (data) messages, and data collection messages.

Figure 5A:
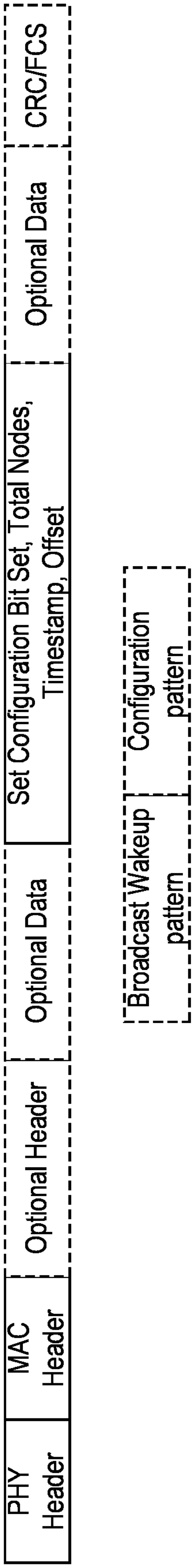
FIG. 5A illustrates an example of a configuration beacon message (Beacon C)

FIG. 5A illustrates an example of a configuration beacon message (Beacon C). As shown, the Beacon C message may include a physical header, a media access control (MAC) header, and/or other optional headers or optional data for the physical layer and/or protocol being used. Depending on the protocol being used, the Beacon C message may also include data correction checks such as cyclic redundancy check (CRC) or frame check sequence (FCS). Further, the Beacon C message may also be encrypted with the methods agreed upon during pairing processes of respective wireless technologies.

The payload of the Beacon C message may include information for use by the wakeup device 402 in initiating system configuration. For instance, to identify the message as being the Beacon C message, the Beacon C message may include a configuration bit set to '1' (or another value denoting the Beacon C message is a configuration message). Further, the Beacon C message may include a timestamp to synchronize system clocks of network devices and to avoid replay attacks. The Beacon C message may further include a total number of devices (e.g., the general sensor devices 206 and the transmit-only devices 202) and optionally an offset value to indicate the beginning of data collection phase.

Responsive to receiving the Beacon C message, the wakeup device 402 responsible for generating wakeup signal, if any, may proceed to configure each of the transmit-only devices 202. The wakeup device 402 may also send a system broadcast wakeup pattern including a pattern to indicate beginning of configuration cycle. This could be used by the other devices to synchronize their clocks.

Figure 5B:
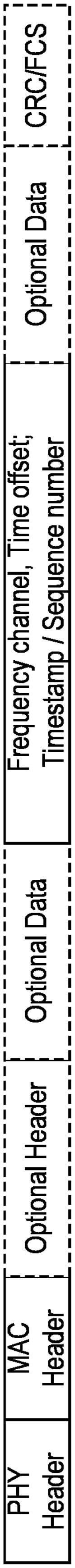
FIG. 5B illustrates an example of a configure sensor (CS) message.

FIG. 5B illustrates an example of a configure sensor (CS) message for general sensor devices 206. These CS messages may be individually sent to general sensor devices 206 to inform the general sensor devices 206 about the frequency channel to be used for data transfer and time offset (with respect to reception of data collection cycle beacon message). When number of devices is small, there could also be one large beacon message with data for all sensors 102. The configuration message may also include its own timestamp or sequence number, e.g., to avoid replay attacks.

Figure 5C:
FIG. 5C illustrates an example of a configure transmit (CT) message for transmit-only devices.

FIG. 5C illustrates an example of a configure transmit (CT) message for transmit-only devices 202. For the transmit-only devices 202, the wakeup signal may include an individual wakeup pattern for each transmit-only device 202. This wakeup pattern may be appended with additional information, such as time offset pattern denoting, from reception of this message or reception of wakeup message, the configuration of data collection with the indicated broadcast pattern. In the first case, the message may also include periodic wakeup offset pattern. Additionally, the wakeup pattern may also be appended with frequency offset and/or a wakeup sequence number pattern (e.g., to avoid replay attacks on wakeup patterns).

The configuration of general sensor devices 206 and transmit-only devices 202 may also occur in parallel when configuration of these two sets is done by two different devices, e.g., by data collector devices 204 and dedicated wakeup devices 402, respectively, for pipelined architectures, or if the data collector device 204 has more than one radio.

Figure 5D:
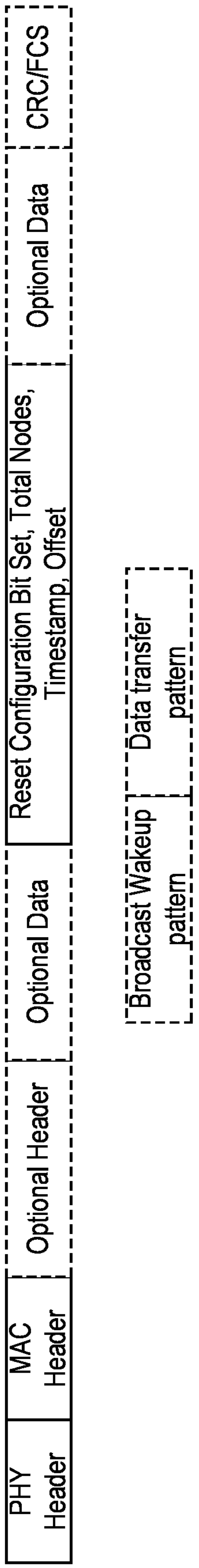
FIG. 5D illustrates an example of a data period beacon message (Beacon D)

FIG. 5D illustrates an example of a data period beacon message (Beacon D). The Beacon D messages may be sent from controller to initiate data collection with configuration bit set to '0' or another value denoting the Beacon D message as a non-configuration message. The remainder of the format and content of the Beacon D messages may be similar to that in the configuration messages. The wakeup device 402 may also send a system broadcast wakeup pattern including a pattern to indicate the beginning of a data transfer cycle. This may be used by devices to synchronize their clocks.

Figure 5E:
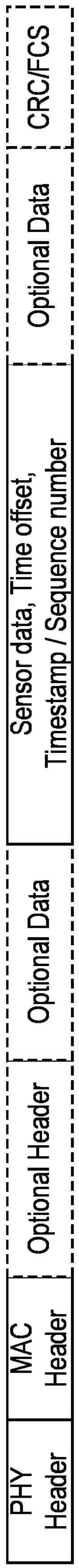
FIG. 5E illustrates an example of a sensor data message (DS)

FIG. 5E illustrates an example of a sensor data message (DS). These sensor data messages may be sent from general sensor devices 206. During the data collection phase, each of the general sensor devices 206 transmits their data as per their assigned offsets to the data collector device 204.

Figure 5F:
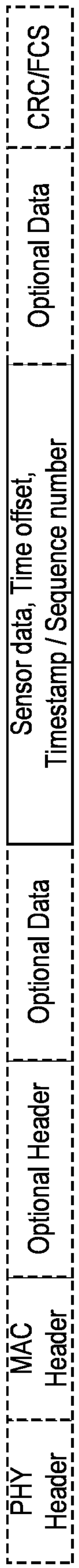
FIG. 5F illustrates an example of a transmit-only data message (DT)

FIG. 5F illustrates an example of a transmit-only data message (DT). For the transmit-only devices 202, the transmit-only devices 202 wakeup periodically as well to transmit based on whitelist combination of frequency channel, power level, antenna, etc., as set by the receiver/collector/wakeup device during configuration phase. The data message could itself conform to standard protocol and hence can have its associated headers and data check bits. The devices may also include their time offsets values that could assist receiver/collector to initiate synchronization as needed.

Depending on application data rate requirements there could be gap between successive data collection cycles denoted by offset in data period beacon.

Figure 5G:
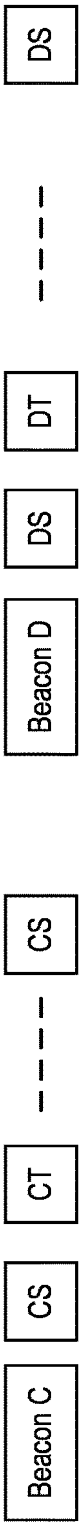
FIG. 5G illustrates an example of periodic message scheduling for data transfer for a no pipeline, single radio receiver architecture.

FIG. 5G illustrates an example of periodic message scheduling for data transfer for a no pipeline, single radio receiver architecture. As shown, in the configuration phase, Beacon C messages are sent (as shown in FIG. 5A), followed by CS messages (as shown in FIG. 5B), followed by CT messages (as shown in FIG. 5C). This pattern may be repeated (e.g., periodically). It should also be noted that the order of the Beacon C, CS, and CT messages is not relevant, and may be sent in orderings other than as shown. In the data phase, the Beacon D messages may be sent (as shown in FIG. 5D), followed by DS messages (as shown in FIG. 5E), followed by DT messages (as shown in FIG. 5F). This pattern may also be repeated (e.g., periodically). It should also be noted that the relative order of the Beacon D, DS, and DT messages may differ from that as shown.

Figure 5H:
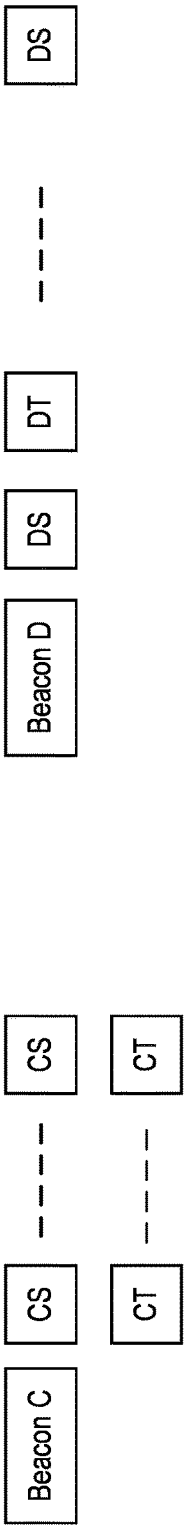
FIG. 5H illustrates an example of periodic message scheduling for data transfer in a no pipeline, single radio receiver architecture with a dedicated wakeup source.

FIG. 5H illustrates an example of periodic message scheduling for data transfer in a no pipeline, single radio receiver architecture with a dedicated wakeup source. Here, a first source (collector/receiver device) sends the Beacon C and CS messages, while another source, the dedicated wakeup source, sends the CT messages. In doing so, the CS and CT messages may be sent concurrently and/or in an overlapping pattern on different frequency channels, speeding up the configuration phase. The data phase, however, is similar to that in the no pipeline, single radio receiver architecture as there is single transceiver 226 at the receiver which can only tune to one frequency channel at a time.

Figure 5I:
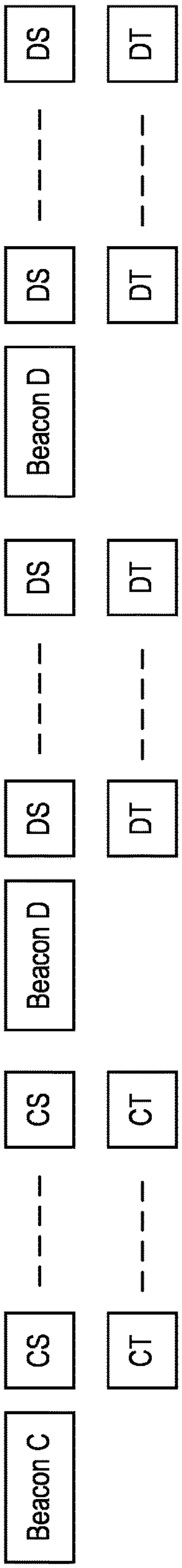
FIG. 5I illustrates an example of periodic message scheduling for data transfer in a pipeline enabled, two separate receivers/single receiver device with two radios architecture.

FIG. 5I illustrates an example of periodic message scheduling for data transfer in a pipeline enabled, two separate receivers/single receiver with two radios architecture. Here again, a first source (collector/receiver) sends the Beacon and CS messages, while another source (collector/receiver) sends the CT messages. Additionally, as two receivers or two radios are used, the first source sends the Beacon D and receives DS messages, while the second source receives the DT messages concurrently.

FIGS. 6A-6G and 7 illustrate an optimized pipeline architecture with data aggregation that may also be provided by the BAN 200. In this variation, the general sensor devices 206 may be scheduled for data communication. In each data communication slot, one of the transmit-only devices 202 may be woken to transmit. This data is received by the next scheduled general sensor devices 206 (or by a dedicated general sensor device 206). That general sensor device 206, in its own slot, then transmits its own data plus the aggregated data from the transmit-only device 202. In this approach, only a single receiver device 302 and/or data collector device 204 may be required for the BAN 200.

The $n^{th}$ transmit-only device 202N may transmit to general sensor device 206(n−1). Then, in the next cycle, the general sensor device 206(n−1) may send its own data along with that of the $n^{th}$ transmit-only device 202. The wakeup pattern may be generated by general sensor device 206 which is going to listen to the corresponding transmit-only device 202.

A separate wakeup device 402 may alternatively be used to generate wakeup patterns for transmit-only devices 202. This wakeup may be required only in the first data transmission cycle, because after that the transmit-only devices 202 may wake themselves up periodically. Further, the receiver device 302 may also transmit a broadcast wakeup pattern at beginning of every data cycle to synchronize the transmit-only devices 202.

Figure 6A:
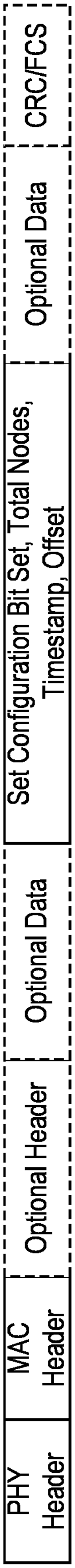
FIG. 6A illustrates an example of a configuration Beacon C message for the architecture including data aggregation.

FIG. 6A illustrates an example of a configuration Beacon C message for the architecture including data aggregation. As shown, the Beacon C message is similar to the Beacon C message without data aggregation.

Figure 6B:
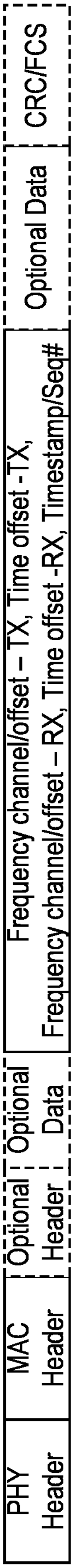
FIG. 6B illustrates an example of a CS message for the architecture including data aggregation.

FIG. 6B illustrates an example of a CS message for the architecture including data aggregation. As compared to the CS message without aggregation, this CS message includes frequency channel/offsets and time offset for transmission as well as for reception.

Figure 6C:
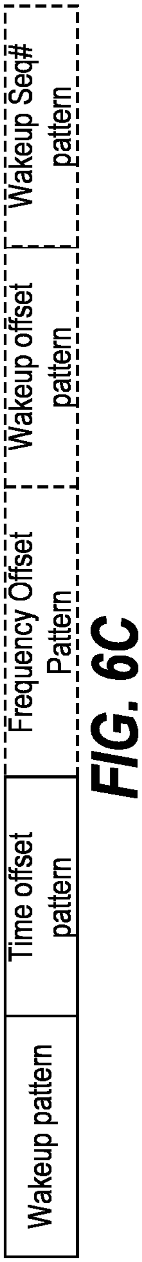
FIG. 6C illustrates an example of a CT for transmit-only devices for the architecture including data aggregation.

FIG. 6C illustrates an example of a CT for transmit-only devices 202 for the architecture including data aggregation. As shown, the CT message is similar to the CT message without data aggregation.

Figure 6D:
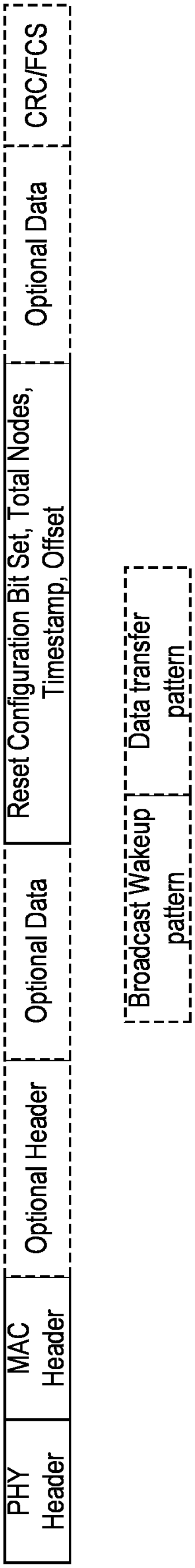
FIG. 6D illustrates an example of a Beacon D for the architecture including data aggregation.

FIG. 6D illustrates an example of a Beacon D for the architecture including data aggregation. As shown, the Beacon D is again similar to the Beacon D without data aggregation.

Figure 6E:
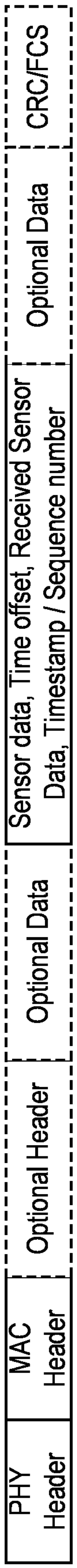
FIG. 6E illustrates an example of a DS for the architecture including data aggregation.

FIG. 6E illustrates an example of a DS for the architecture including data aggregation. As shown, this DS message additionally includes received sensor data from a transmit-only device 202, in addition to the sensor data for the general sensor device 206 itself.

Figure 6F:
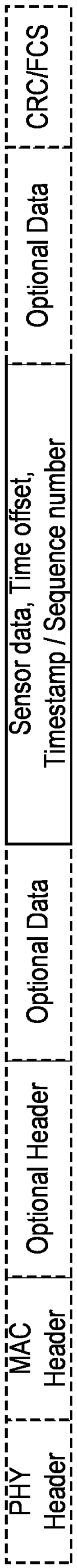
FIG. 6F illustrates an example of a transmit-only data message (DT) for the architecture including data aggregation.

FIG. 6F illustrates an example of a transmit-only data message (DT) for the architecture including data aggregation. This message is similar to the DS message for the architecture without data aggregation.

Figure 6G:
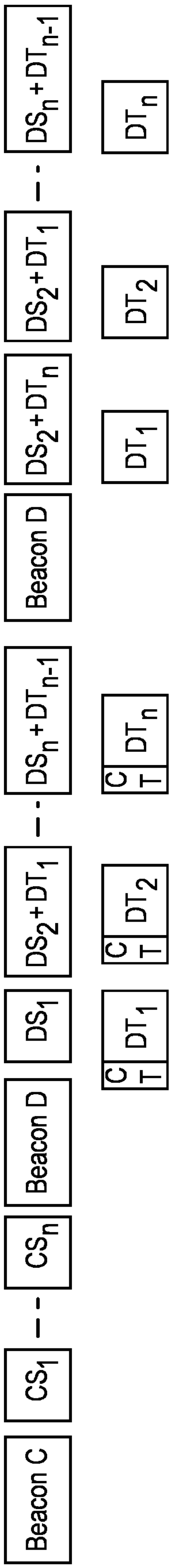
FIG. 6G illustrates an example of periodic message scheduling for data transfer in a pipeline enabled, single receiver architecture with data aggregation.

FIG. 6G illustrates an example of periodic message scheduling for data transfer in a pipeline enabled, single receiver architecture with data aggregation. As shown for the configuration phase, a first source begins by sending the Beacon C messages (as shown in FIG. 6A) and the CS messages (as shown in FIG. 6B) to configure each sensor when to wakeup. Once the configuration phase is complete, in the data collection phase the first source sends source sends the Beacon D messages (as shown in FIG. 6D) to signal beginning of data collection phase. Each sensor 102 then sends DS messages (as shown in FIG. 6E) including data aggregation (e.g., including data from the previous DT messages of the corresponding transmit-only devices 202) during their pre-assigned slot while they wakeup in previous slot to receive data from transmit-only device 202 which they transmit in their assigned slot. In every slot while one of the sensor device is transmitting DS message to collector/receiver, the alternate source (collector/receiver/wakeup/general sensor device) wakes up a transmit-only device 202 using CT messages (as shown in FIG. 6C), which then sends DT message (as shown in FIG. 6F) concurrently to next schedule sensor device (which is already in listening mode on transmit-only device 202 frequency channel). The first set of DT messages may also be combined with CT messages (as shown in FIG. 6C) to allow for the setting of the wakeup patterns for the transmit-only devices 202. For subsequent CT messages, transmit-only devices 202 knows when to wakeup periodically as configured using CT messages. To ensure better synchronicity, these CT messages can be repeated in occasionally during data collection cycles.

Figure 7:
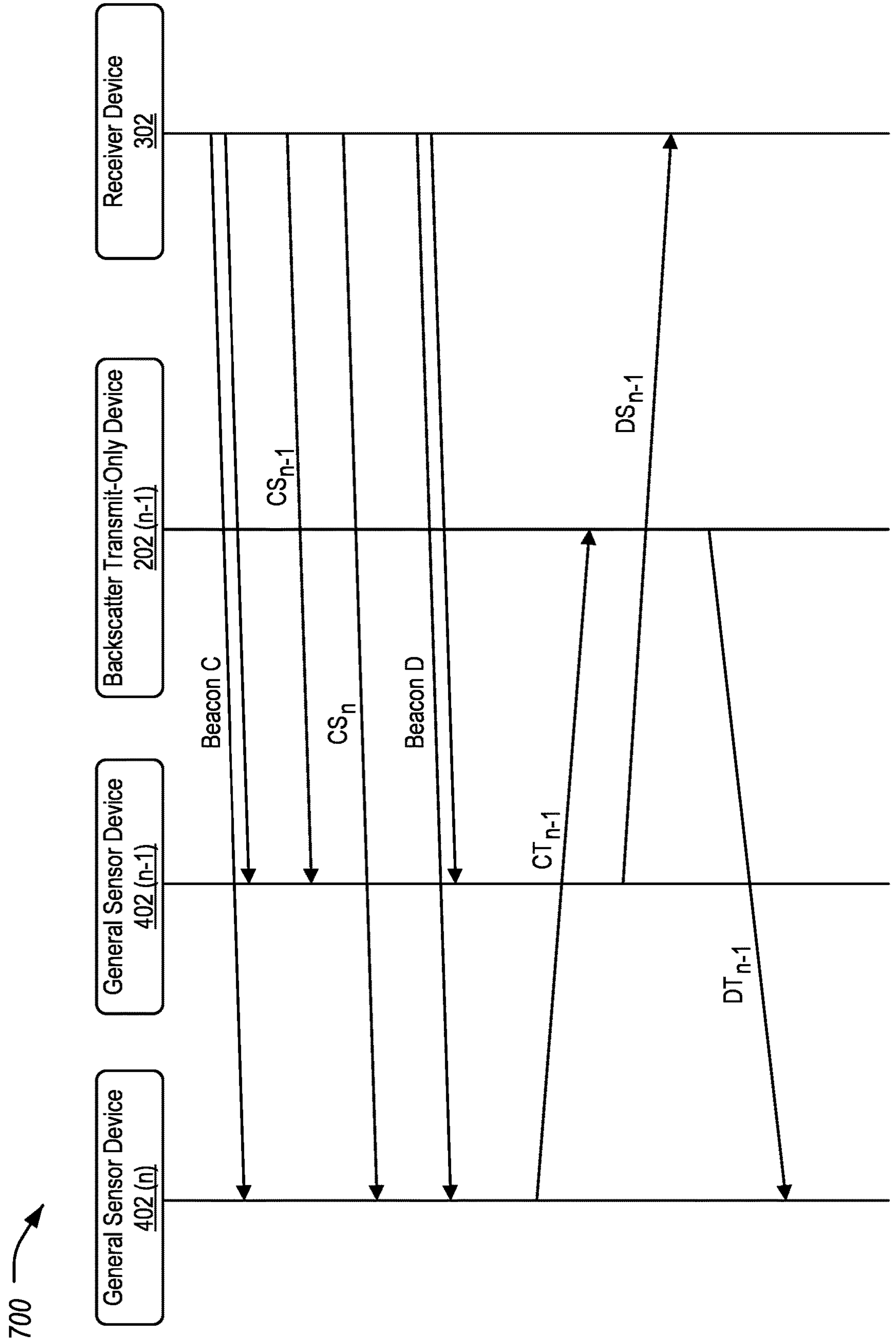
FIG. 7 illustrates an example of periodic message scheduling for data transfer for the architecture including data aggregation.

FIG. 7 illustrates an example data flow diagram 700 of the periodic message scheduling for data transfer in a pipeline enabled, single receiver architecture with data aggregation. First, in the configuration phase, the receiver device 302 sends the Beacon C messages which are received by each of the general sensor devices 206. Next, the receiver device 302 sends the $CS_1$-$CS_n$ messages, which are received by the corresponding general sensor devices 206 (1 through n). Once that phase is complete, in the data collection phase the receiver device 302 sends Beacon D messages to the sensor general sensor devices 206. The general sensor devices 206, in turn, send the CT messages to the transmit-only devices 202 to configure the transmit-only devices 202. The transmit-only devices 202 then send DT messages to the general sensor devices 206 in response, e.g., according to the configured time offsets. The content of these DT messages may then be compiled into the DS messages sent from the general sensor devices 206 to the receiver device 302.

It should be noted that the pipeline architectures may be especially useful when the number of transmit-only devices 202 is equal to or less than the number of general sensor devices 206 in the BAN 200.

It should also be noted that, to achieve power optimization, the sensor devices may be equipped with a low power wakeup receiver 214. In this case, the devices may take turns toggling between general sensor device 206 mode and transmit-only device 202 modes. In an example, a general sensor device 206 which is transmitting more frequently may switch itself to transmit-only device 202 mode and may use all transmit-only time slots for data communication in the pipelined architecture to achieve power optimization.

It should further be noted that in all the aforementioned architectures, an additional guard band may be used before every transmit-only device 202 when they are explicitly woken up to receive wakeup signal pattern. In some examples, the devices 202, 204, 206 may also enable data encoding in which case they send either processed data or only differential data in their time slots to optimize their own respective overall transmissions.

Thus, sensors 102 with transmit-only radios may be utilized in a BAN 200 to provide an order of magnitude of power savings for wireless communication. To support various quality of service requirements, the management of the transmit-only devices 202 may be accomplished using various architectures, including: a no pipeline, single radio receiver architecture; a no pipeline, single radio receiver architecture with a dedicated wakeup source; pipeline enabled, a two receiver/receiver with two radios architecture; and a pipeline enabled, single receiver architecture with data aggregation.

Figure 8:
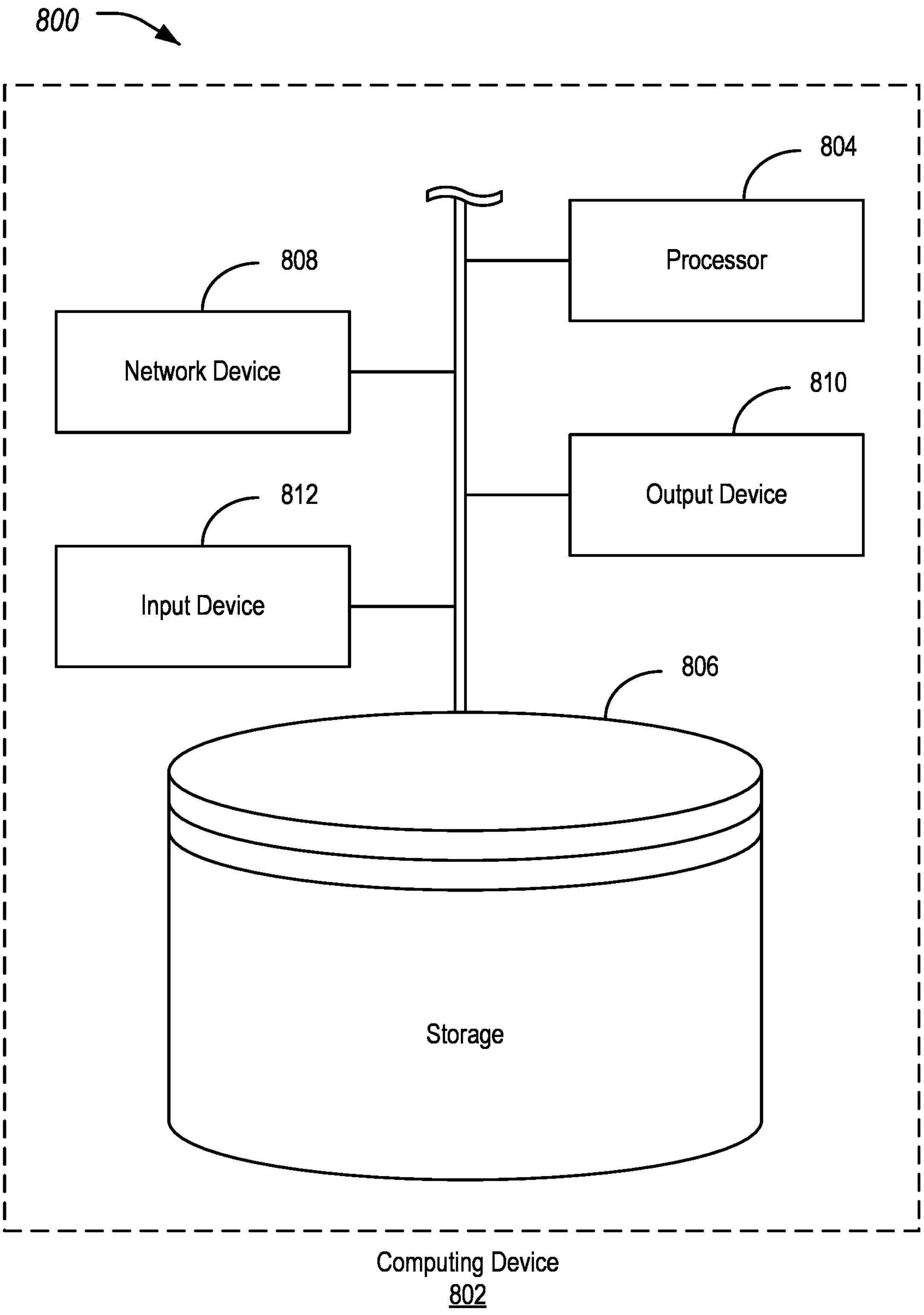
FIG. 8 illustrates an example of a computing device for use in the body area network architectures.

FIG. 8 illustrates an example 800 of a computing device 802 for use in the BAN 200 architectures. Referring to FIG. 8, and with reference to FIGS. 1-7, the sensors 102, transmit-only devices 202, data collector devices 204, general sensor devices 206, receiver devices 302, wakeup devices 402, etc., may be examples of such computing devices 802. As shown, the computing device 802 includes a processor 804 that is operatively connected to a storage 806, a network device 808, an output device 810, and an input device 812. It should be noted that this is merely an example, and computing devices 802 with more, fewer, or different components may be used.

The processor 804 may include one or more integrated circuits that implement the functionality of a central processing unit (CPU) and/or graphics processing unit (GPU). In some examples, the processors 804 are a system on a chip (SoC) that integrates the functionality of the CPU and GPU. The SoC may optionally include other components such as, for example, the storage 806 and the network device 808 into a single integrated device. In other examples, the CPU and GPU are connected to each other via a peripheral connection device such as peripheral component interconnect (PCI) express or another suitable peripheral data connection. In one example, the CPU is a commercially available central processing device that implements an instruction set such as one of the x86, ARM, Power, or microprocessor without interlocked pipeline stage (MIPS) instruction set families.

Regardless of the specifics, during operation the processor 804 executes stored program instructions that are retrieved from the storage 806. The stored program instructions, accordingly, include software that controls the operation of the processors 804 to perform the operations described herein. The storage 806 may include both non-volatile memory and volatile memory devices. The non-volatile memory includes solid-state memories, such as not and (NAND) flash memory, magnetic and optical storage media, or any other suitable data storage device that retains data when the system is deactivated or loses electrical power. The volatile memory includes static and dynamic random-access memory (RAM) that stores program instructions and data during operation of the system 100.

The GPU may include hardware and software for display of at least two-dimensional (2D) and optionally 3D graphics to the output device 810. The output device 810 may include a graphical or visual display device, such as an electronic display screen, projector, printer, or any other suitable device that reproduces a graphical display. As another example, the output device 810 may include an audio device, such as a loudspeaker or headphone. As yet a further example, the output device 810 may include a tactile device, such as a mechanically raiseable device that may, in an example, be configured to display braille or another physical output that may be touched to provide information to a user.

The input device 812 may include any of various devices that enable the computing device 802 to receive control input from users. Examples of suitable input devices that receive human interface inputs may include keyboards, mice, trackballs, touchscreens, voice input devices, graphics tablets, and the like.

The network devices 808 may each include any of various devices that enable the devices to send and/or receive data from external devices over networks. Examples of suitable network devices 808 include an Ethernet interface, a Wi-Fi transceiver, a cellular transceiver, or a BLUETOOTH or BLE transceiver, UWB transceiver, or other network adapter or peripheral interconnection device that receives data from another computer or external data storage device, which can be useful for receiving large sets of data in an efficient manner.

The processes, methods, or algorithms disclosed herein can be deliverable to/implemented by a processing device, controller, or computer, which can include any existing programmable electronic control unit or dedicated electronic control unit. Similarly, the processes, methods, or algorithms can be stored as data and instructions executable by a controller or computer in many forms including, but not limited to, information permanently stored on non-writable storage media such as read-only memory (ROM) devices and information alterably stored on writeable storage media such as floppy disks, magnetic tapes, compact discs (CDs), RAM devices, and other magnetic and optical media. The processes, methods, or algorithms can also be implemented in a software executable object. Alternatively, the processes, methods, or algorithms can be embodied in whole or in part using suitable hardware components, such as application specific integrated circuit (ASIC), field-programmable gate array (FPGA), state machines, controllers or other hardware components or devices, or a combination of hardware, software and firmware components.

While exemplary embodiments are described above, it is not intended that these embodiments describe all possible forms encompassed by the claims. The words used in the specification are words of description rather than limitation, and it is understood that various changes can be made without departing from the spirit and scope of the disclosure. As previously described, the features of various embodiments can be combined to form further embodiments of the invention that may not be explicitly described or illustrated. While various embodiments could have been described as providing advantages or being preferred over other embodiments or prior art implementations with respect to one or more desired characteristics, those of ordinary skill in the art recognize that one or more features or characteristics can be compromised to achieve desired overall system attributes, which depend on the specific application and implementation. These attributes can include, but are not limited to strength, durability, life cycle, marketability, appearance, packaging, size, serviceability, weight, manufacturability, ease of assembly, etc. As such, to the extent any embodiments are described as less desirable than other embodiments or prior art implementations with respect to one or more characteristics, these embodiments are not outside the scope of the disclosure and can be desirable for particular applications.

What is claimed is:

1. A method for configuring and utilizing a body area network (BAN) including a plurality of transmit-only devices, each including a wakeup receiver, a transmitter, and an antenna switching circuit configured to switch between a transmit mode in which the transmitter is utilized to send sensor data messages and a receiving mode in which the wakeup receiver is configured to receive wakeup signals and default to when not transmitting, comprising:

in a configuration phase, sending a wakeup signal including configuration information for scheduling the plurality of transmit-only devices such that during a data collection phase each of the plurality of transmit-only devices is configured to transmit in an individually-assigned time slot; and in the data collection phase, receiving, to a data collector device from the plurality of transmit-only devices, sensor data messages including sensor data from the transmit-only devices, the sensor data messages being scheduled according to the configuration phase.

2. The method of claim 1, further comprising:

in the data collection phase, sending data period beacon messages for scheduling the plurality of transmit-only devices to indicate a beginning of a data transfer cycle.

3. The method of claim 1, further comprising:

in the configuration phase, sending the configuration information for scheduling a plurality of general sensor devices having transmit and receive functionality, such that during the data collection phase each of the plurality of general sensor devices is also configured to transmit in an individually-assigned time slot.

4. The method of claim 3, further comprising in the data collection phase:

receiving, to each one of the general sensor devices from a respective one of the plurality of transmit-only devices, transmit-only sensor data messages including received sensor data from the transmit-only devices; and sending, to the data collector device from the general sensor devices, general device sensor data messages including sensor data captured by the general sensor devices and also the received sensor data from the transmit-only devices.

5. The method of claim 4, wherein the configuration information for scheduling the plurality of general sensor devices is sent in a different channel from the configuration information for scheduling the plurality of transmit-only devices.

6. The method of claim 4, wherein the transmit-only sensor data messages are sent in a different channel from the general device sensor data messages.

7. The method of claim 1, wherein the configuration information includes a timestamp to synchronize system clocks of the plurality of transmit-only devices.

8. The method of claim 1, wherein the configuration information includes a total number of the plurality of transmit-only devices and/or an offset value to indicate a beginning of the data collection phase.

9. The method of claim 1, wherein the configuration information is sent from the data collector device.

10. The method of claim 1, wherein the configuration information is sent from a wakeup device.

11. A system for configuring and utilizing a body area network (BAN), comprising:

a plurality of transmit-only devices, each including a wakeup receiver, a transmitter, and an antenna switching circuit configured to switch between a transmit mode in which the transmitter is utilized to send sensor data messages and a receiving mode in which the wakeup receiver is configured to receive wakeup signals and default to when not transmitting; and a data collector device, wherein in a configuration phase, the plurality of transmit-only devices are configured to receive, via the wakeup receiver, a wakeup signal including configuration information for scheduling transmissions of the plurality of transmit-only devices, such that during a data collection phase each of the plurality of transmit-only devices is configured to transmit in an individually-assigned time slot, and in the data collection phase, the data collector device is configured to receive, from the plurality of transmit-only devices, sensor data messages including sensor data from the transmit-only devices, the sensor data messages being scheduled according to the configuration phase.

12. The system of claim 11, wherein in the data collection phase, the plurality of transmit-only devices are configured to send the sensor data messages responsive to receipt of data period beacon messages, the data period beacon messages indicating a beginning of a data transfer cycle.

13. The system of claim 11, further comprising:

a plurality of general sensor devices having transmit and receive functionality, wherein in the configuration phase, the plurality of general sensor devices are configured to receive the configuration information to schedule the plurality of general sensor devices to transmit in individually-assigned time slots of the data collection phase.

14. The system of claim 13, wherein in the data collection phase:

each one of the general sensor devices is configured to:

receive, from a respective one of the plurality of transmit-only devices, transmit-only sensor data messages including received sensor data from the respective one of the transmit-only devices; and send, to the data collector device, general device sensor data messages including sensor data captured by the general sensor devices and also the received sensor data from the transmit-only devices.

15. The system of claim 14, wherein the configuration information for scheduling the plurality of general sensor devices is sent in a different channel from the configuration information for scheduling the plurality of transmit-only devices.

16. The system of claim 14, wherein the transmit-only sensor data messages are sent in a different channel from the general device sensor data messages.

17. The system of claim 11, wherein the configuration information includes a timestamp to synchronize system clocks of the plurality of transmit-only devices.

18. The system of claim 11, wherein the configuration information includes a total number of the plurality of transmit-only devices and/or an offset value to indicate a beginning of the data collection phase.

19. The system of claim 11, wherein the configuration information is sent from the data collector device.

20. The system of claim 11, wherein the configuration information is sent from a wakeup device.

* * * * *